United States Patent [19]

Lautenschläger et al.

[11] Patent Number: 4,460,598
[45] Date of Patent: Jul. 17, 1984

[54] TRIPHENYLIMIDAZOLYLOXYALKANOIC ACIDS AND THEIR DERIVATIVES AND A PROCESS FOR THE TREATMENT OF THROMBOEMBOLIC, INFLAMMATORY AND/OR ATHERIOSCLEROTIC DISEASES

[75] Inventors: Hans-Heiner Lautenschläger, Pulheim-Stommeln; André Welter, Pulheim; Gerd Hilboll; Johannes Winkelmann, both of Cologne; Gerrit Prop, Pulheim; Axel Brekle, Frechen; Ottfried Zierenberg, Cologne, all of Fed. Rep. of Germany

[73] Assignee: A. Nattermann & Cie GMBH, Cologne, Fed. Rep. of Germany

[21] Appl. No.: 516,938

[22] Filed: Jul. 25, 1983

[30] Foreign Application Priority Data
Jul. 29, 1982 [DE] Fed. Rep. of Germany ....... 3228271

[51] Int. Cl.³ ................. C07D 233/70; A61K 31/415
[52] U.S. Cl. ............................... 424/273 R; 548/336; 548/337
[58] Field of Search ............................ 548/336, 337; 424/273 R

[56] References Cited
U.S. PATENT DOCUMENTS
3,636,003 1/1972 Doebel et al. ............... 548/337

*Primary Examiner*—Robert W. Ramsuer
*Attorney, Agent, or Firm*—Pearne, Gordon, Sessions, McCoy, Granger & Tilberry

[57] ABSTRACT

The invention relates to new triphenylimidazolyloxyalkanoic acids of the general formula I

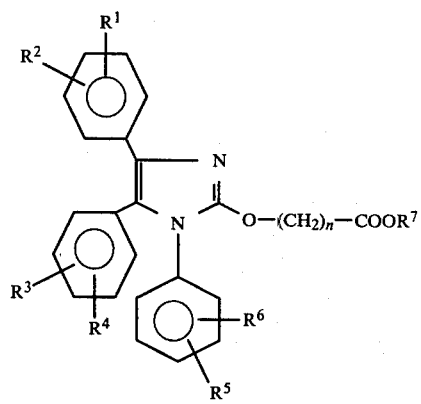

and a process for the treatment of thromboembolic, inflammatory and/or atherosclerotic diseases in humans by using the same.

21 Claims, No Drawings

TRIPHENYLIMIDAZOLYLOXYALKANOIC ACIDS AND THEIR DERIVATIVES AND A PROCESS FOR THE TREATMENT OF THROMBOEMBOLIC, INFLAMMATORY AND/OR ATHERIOSCLEROTIC DISEASES

The present invention relates to new triphenylimidazolylalkanoic acids and their derivatives, processes for their preparation and their use as the active compound in medicaments.

The compounds according to the invention correspond to the general formula I

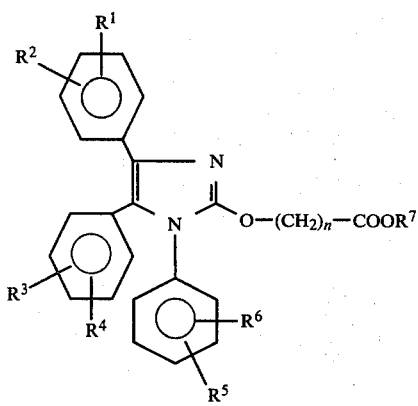

wherein n denotes an integer from 1 to 10, while $R^1$, $R^2$, $R^3$, $R^4$, $R^5$ and $R^6$ which are identical or different from each other, are members selected from the group consisting of hydrogen, the halogens, alkyl, preferably $C_{1-4}$—alkyl, alkoxy, preferably $C_{1-4}$—alkoxy, and trifluoromethyl, and once or several of the groupments $R^1$ and $R^2$, $R^3$ and $R^4$, and $R^5$ and $R^6$ together a methylenedioxy group. Particularly suitable and, therefor, preferred are hydrogen, methyl, ethyl, n— and isopropyl, fluorine, chlorine, bromine, methoxy and ethoxy, hydrogen being most preferred. $R^7$ in formula I is a member selected from the group consisting of hydrogen, the alkali metal ions, the straight-chain or branched alkyl group with 1 to 6 carbon atoms, such as, for example, methyl, ethyl, propyl, isopropyl, butyl or isobutyl, and the benzyl group. The methyl and the ethyl groups being the preferred alkyl groups.

Examples of compounds according to the invention are: 1,4,5-triphenylimidazol-2-yloxyacetic acid, 4-(1,4,5-triphenylimidazol-2-yloxy)-butyric acid, 5-(1,4,5-triphenylimidazol-2-yloxy)-valeric acid, 6-(1,4,5-triphenylimidazol-2-yloxy)-caproic acid, 7-(1,4,5-triphenylimidazol2-yloxy)oenanthic acid, 8-(1,4,5-triphenylimidazol-2-yloxy)-caprylic acid, methyl 8-(1,4,5-triphenylimidazol-2-yloxy)-caprylate, ethyl 8-(1,4,5-triphenylimidazol-2-yloxy)-caprylate, 8-[4,5-diphenyl-1-(4-methoxyphenyl)-imidazol-2-yloxy]-caprylic acid, 8-[1-(4-chlorophenyl)-4,5-diphenylimidazol-2-yloxy]-caprylic acid, 8-[4,5-diphenyl-1-(4-methylphenyl)-imidazol-2-yloxy]-caprylic acid, 8-[4,5-diphenyl-1-(2-fluorophenyl)-imidazol-2-yloxy]-caprylic acid, 8-[4,5-bis-(4-chlorophenyl)-1-phenylimidazol-2-yloxy]-caprylic acid, 8-[4,5-bis-(4-fluorophenyl)-1-phenyl-imidazol-2-yloxy]-caprylic acid, 8-[4,5-bis-(4-methoxyphenyl)-1-phenyl-imidazol-2-yloxy]-caprylic acid, 8-[1,4,5-tris-(4-chlorophenyl)-imidazol-2-yloxy]-caprylic acid, 8-[1-(3,4-dimethoxyphenyl)-4,5-diphenyl-imidazol-2-yloxy]-caprylic acid, 9-(1,4,5-triphenylimidazol-2-yloxy)-pelargonic acid, 10-(1,4,5-triphenylimidazol-2-yloxy)-caprylic acid and 11-(1,4,5-triphenylimidazol-2-yloxy)-undecanoic acid.

The compounds according to the invention display interesting pharmacological properties, in particular antithrombotic, anti-inflammatory, antiatherosclerotic and lipid-lowering activity, and have an excellent tolerance. They can accordingly be used as active agent, in particular, in processes for the treatment of thromboembolic, inflammatory and atherosclerotic diseases in humans and diseases connected with lipid metabolism in humans. In addition, the compounds of the formula I have the advantage of low toxicity.

The compounds according to the invention are prepared by a process know as such wherein a 4-imidazolin-2-one of the general formula II

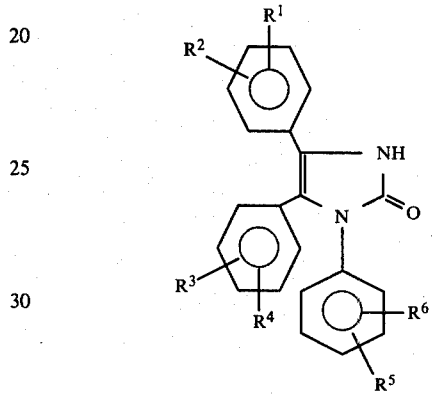

wherein $R^1$, $R^2$, $R^3$, $R^4$, $R^5$ and $R^6$ have the meanings given in formula I, is converted into the corresponding alkali metal salt in an inert organic solvent, such as, for example, dimethylformamide or N,N-dimethylacetamide, by addition of an auxiliary base, such as, for example, sodium hydride, potassium hydride or organolithium compounds, and this salt is reacted with an alkylating agent of the general formula III $$X—(CH_2)_n—COOR^7 \qquad III$$

wherein n and $R^7$ have the meanings given in formula I and X is a halogen or a tosyl radical. The resulting esters are separated, for example by column chromatography or recrystallisation, from the isomers formed as a result of N-alkylation of II.

The starting compounds of the formula II are prepared by or analogously to known processes, for example Org. Synth. Coll. Vol. II, 231, H. Ahlbrecht and H. Hanisch, Synthesis 1973, 109, H. G. Aurich, Liebigs Ann. Chem. 732, 195 (1970), B. Krieg and H. Lautenschläger, Liebigs Ann. Chem. 1976, 208, B. Krieg and H. Lautenschläger, Liebigs Ann. Chem. 1976, 1471, and Y. A. Baskakov et al., Russian Patent No. 389,096 and C.A. 79, 126,502 (1973).

The resulting esters of the formula I can be converted into the corresponding alkali metal salt of the formula I by customary processes, for example by reaction with an alkali metal hydroxide in aqueous, aqueous-organic or organic reaction media, such as, for example, water, alcohols or ethers or mixtures thereof, and into the acids of the formula I by subsequent addition of a mineral acid.

Conversely, the esters of the formula I can be prepared from the acids of the formula I and the alkali metal salts of the formula I by processes customary in organic chemistry, thus, for example, by treatment of the acids with the corresponding alcohols, with addition of a condensing agent, such as dicyclohexylcarbodiimide, and, for example, by trans-esterification with formic acid esters or acetic acid esters, or by alkylation of the alkali metal salts of the formula I with the corresponding alkyl halides, alkyl sulphates and the like in inert solvents.

The preparation of the compounds of the formula I is illustrated by the following equation:

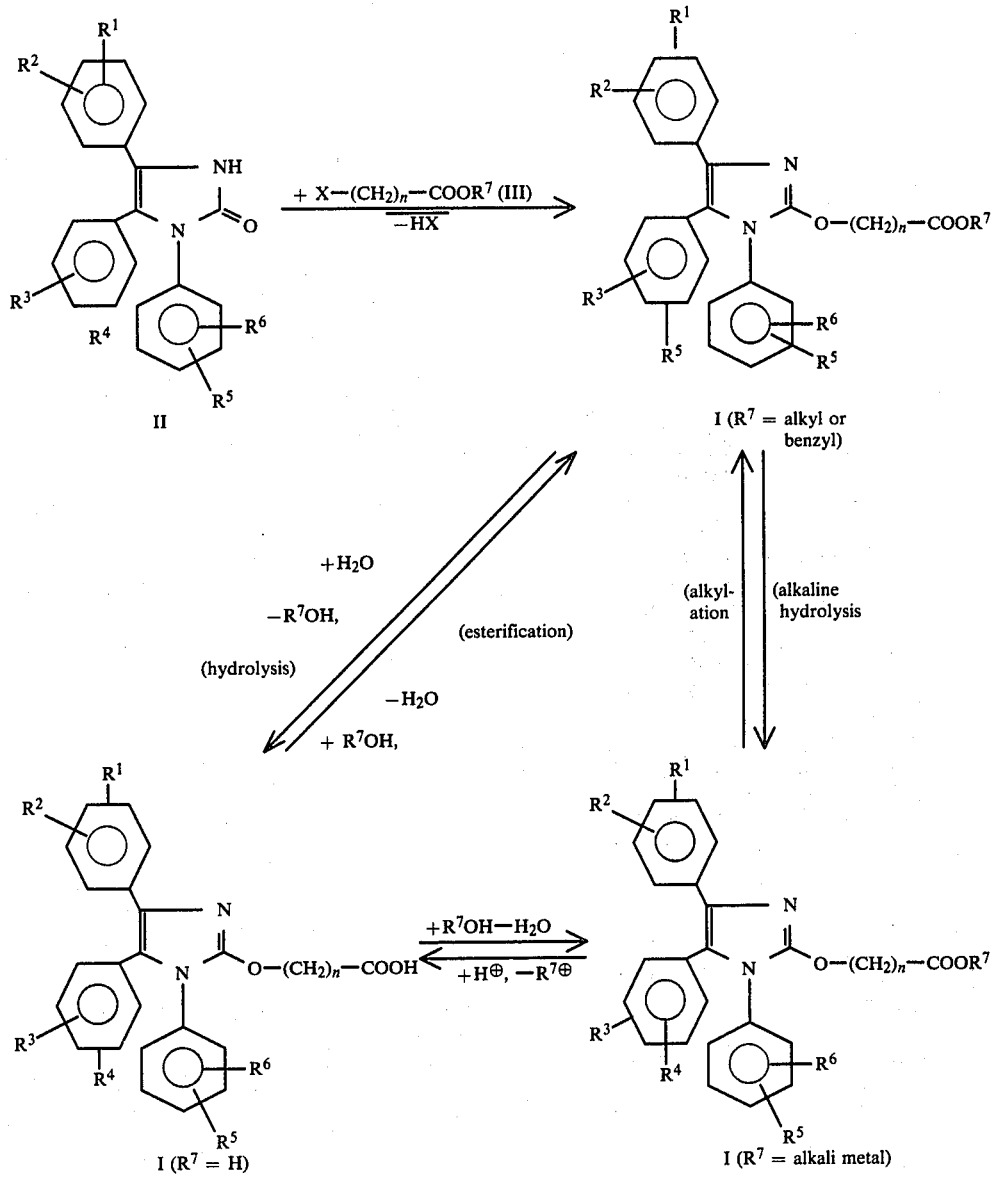

Examples of suitable phenyl radicals substituted by $R^1$, $R^2$, $R^3$, $R^4$, $R^5$ and $R^6$ in the compounds I are: phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-ethoxyphenyl, 3-ethoxyphenyl, 4-ethoxyphenyl, 2-methylphenyl, 3-methylphenyl, 4-methylphenyl, 2-trifluoromethylphenyl, 3-trifluoromethylphenyl, 4-trifluoromethylphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl and 3,4-methylenedioxyphenyl.

Examples of suitable alkylating agents of the formula III are the esters of the following ω-halogenoalkanoic acids: chloroacetic acid, bromoacetic acid, iodoacetic acid, 3-chloropropionic acid, 3-bromopropionic acid, 3-iodopropionic acid, 4-chlorobutyric acid, 4-bromobutyric acid, 4-iodobutyric acid, 5-chlorovaleric acid, 5-bromovaleric acid, 5-iodovaleric acid, 6-chlorocaproic acid, 6-bromocaproic acid, 6-iodocaproic acid, 7-chlorooenanthic acid, 7-bromooenanthic acid, 7-iodooenanthic acid, 8-chlorocaprylic acid, 8- bromocaprylic acid, 8-iodocaprylic acid, 9-chloropelargonic acid, 9-bromopelargonic acid, 9-iodopelargonic acid, 10-chlorocapric acid, 10-bromocapric acid, 10-iodocapric acid, 11-chloroundecanoic acid, 11-bromoundecanoic acid and 11-iodoundecanoic acid. The alcohols $R^7OH$ are preferably those with a straight-chain or secondary-branched saturated hydrocarbon radical with 1-6 carbon atoms, such as, for example, methanol, ethanol, propanol, isopropanol, butanol, pentanol and hexanol, or benzyl alcohol.

Examples which may be mentioned of alkylating agents for converting the alkali metal salts I into the corresponding esters are: diazomethane, dimethyl sulphate, chloromethane, bromomethane, iodomethane, chloroethane, bromoethane, iodoethane, benzyl chloride and benzyl bromide.

The present invention also relates to processes for the treatment of thromboembolic, inflammatory and/or atheriosclerotic diseases in humans by administering to humans suffering from such diseases a compound of formula I or, respectively a pharmaceutical product which contains the new triphenylimidazolyloxyalkanoic acid derivatives in the form of their free acids or as salts with pharmacologically acceptable bases or in the form of their esters. The pharmaceutical products according to the invention are those for enteral, such as oral or rectal, or parenteral administration and contain the pharmaceutical active compounds by themselves or together with a customary pharmaceutically useful excipient. The pharmaceutical formulation of the active compound is advantageously in the form of individual doses appropriate for the desired administration, such as, for example, tablets, dragees, capsules, suppositories, granules, solutions, emulsions or suspension. The dosage of the compounds is usually between 1 and 1,000 mg per dose, preferably between 10 and 100 mg per dose, and can be administered once or several times, preferably two to three times, daily.

The preparation of the compounds according to the invention is illustrated in more detail by the examples which follow.

The melting points given were measured with a Büchi 510 melting point determination apparatus and are uncorrected. The IR spectra were recorded with a Nicolet NIC-3600 instrument and the mass spectra with a Varian MAT-311A (70 ev) instrument.

EXAMPLE 1

Methyl-8-(1,4,5-triphenylimidazol-2-yloxy)caprylate.

18 g of an 80% strength sodium hydride/mineral oil suspension are washed with n-pentane and added to a mixture of 189 g of 1,4,5-triphenyl-4-imidazolin-2-one in 1,200 ml of dry dimethylformamide. The mixture is stirred, first at room temperature and then under reflux, until the evolution of hydrogen has ended. 142 g of methyl 8-bromooctanoate are added dropwise at the reflux temperature. The mixture is heated further at this temperature for about 3 hours, cooled, diluted with water and extracted with chloroform. The chloroform solution is washed successively with water, 5% strength sodium bicarbonate solution and water, dried over sodium sulphate and concentrated in vacuo. The residue is purified by column chromatography (silica gel/hexane/ethyl acetate).

Yield: 58 g of melting point 85° C.,
IR (in KBr): 1740 cm$^{-1}$.

EXAMPLE 2

Preparation of ethyl-4-(1,4,5-triphenylimidazol-2-yloxy)-butyrate, as described in Example 1, from 36.5 g of a 35% strength potassium hydride/mineral oil suspension, 100 g of 1,4,5-triphenyl-4-imidazolin-2-one, 850 ml of dimethylformamide and 48 g of ethyl 4-chlorobutyrate. Purification by column chromatography (silica gel/hexane/ethyl acetate).

Yield: 23.8 g of melting point 107°-109° C.
IR (in KBr): 1740 cm$^{-1}$.

EXAMPLE 3

Preparation of ethyl-5-(1,4,5-triphenylimidazol-2-yloxy)-valerate, as described in Example 1, from 9.6 g of an 80% strength sodium hydride/mineral oil suspension, 100 g of 1,4,5-triphenyl-4-imidazolin-2-one, 500 ml of dimethylformamide and 67 g of ethyl 5-bromovalerate. Purification by column chromatography (silica gel//hexane/ethyl acetate).

Yield: 19.6 g of melting point 84° C.,
IR (in KBr): 1724 cm$^{-1}$.

EXAMPLE 4

Preparation of ethyl-6-(1,4,5-triphenylimidazol-2-yloxy)-caproate, as described in Example 1 from 33.9 g of a 35% strength potassium hydride/mineral oil suspension, 93 g of 1,4,5-triphenyl-4-imidazolin-2-one, 850 ml of dimethylformamide and 66.9 g of ethyl 6-bromocaproate. Purification by column chromatography (silica gel//hexane/ethyl acetate).

Yield: 28.6 g of melting point 102°-103° C.,
IR (in KBr): 1726 cm$^{-1}$.

EXAMPLE 5

Preparation of ethyl-7-(1,4,5-triphenylimidazol-2-yloxy)-oenanthate, as described in Example 1 from 3.7 g of a 35% strength potassium hydride/mineral oil suspension, 10 g of 1,4,5-triphenyl-4-imidazolin-2-one, 300 ml of dimethylformamide and 7.6 g of ethyl-7-chlorooenanthate. Purification by column chromatography (silica gel//hexane/ethyl acetate).

Yield: 4.3 g of melting point 78°-81° C.,
IR (in KBr): 1727 cm$^{-1}$.

EXAMPLE 6

Preparation of methyl-8-[4,5-diphenyl-1-(4-methoxyphenyl)-imidazol-2-yloxy]-caprylate, as described in Example 1 from 17.6 g of a 35% strength potassium hydride/mineral oil suspension, 53 g of 4,5-diphenyl-1-(4-methoxyphenyl)-4-imidazolin-2-one, 300 ml of dimethylformamide and 37 g of methyl-8-bromocaprylate. Purification by column chromatography (silica gel//hexane/ethyl acetate).

Yield: 25 g of melting point 68°-70° C.,
IR (in KBr): 1732 cm$^{-1}$.

EXAMPLE 7

Preparation of methyl-8-[1-(4-chlorophenyl)-4,5-diphenylimidazol-2-yloxy]-caprylate, as described in Example 1 from 18.8 g of a 35% strength potassium hydride/mineral oil suspension, 57 g of 1-(4-chlorophenyl)-4,5-diphenyl-4-imidazolin-2-one, 300 ml of dimethylformamide and 39 g of methyl 8-bromocaprylate. Purification by column chromatography (silica gel//hexane/ethyl acetate).

Yield: 17.2 g of melting point 89°-91° C.,
IR (in KBr): 1734 cm$^{-1}$.

EXAMPLE 8

Preparation of methyl-8-[4,5-diphenyl-1-(4-methylphenyl)-imidazol-2-yloxy]-caprylate, as described in Example 1 from 26 g of a 35% strength potassium hydride/mineral oil suspension, 54 g of 4,5-diphenyl-1-(4-methylphenyl)-4-imidazolin-2-one, 400 ml of dimethylformamide and 72 g of methyl 8-bromocaprylate. Purification by column chromatography (silica gel//hexane/ethyl acetate).

Yield: 11 g of melting point 108°–110° C.,
IR (in KBr): 1746 cm$^{-1}$.

EXAMPLE 9

Preparation of methyl-8-[4,5-diphenyl-1-(2-fluorophenyl)-imidazol-2-yloxy]-caprylate, as described in Example 1 from 6.8 g of an 80% strength sodium hydride/mineral oil suspension, 74 g of 4,5-diphenyl-1-(2-fluorophenyl)-4-imidazolin-2-one, 500 ml of dimethylformamide and 53 g of methyl 8-bromocaprylate. Purification by column chromatography (silica gel//hexane/ethyl acetate).

Yield: 21 g of melting point 78° C.,
IR (in KBr): 1736 cm$^{-1}$.

EXAMPLE 10

Preparation of methyl-8-[4,5-bis-(4-chlorophenyl)-1-phenyl-imidazol-2-yloxy]-caprylate, as described in Example 1, from: 5.6 g of a 80% strength sodium hydride/mineral oil suspension, 70 g of 4,5-bis-(4-chlorophenyl)-1-phenyl-4-imidazolin-2-one, 500 of dimethylformamide and 44 g of methyl 8-bromocaprylate. Purification by column chromatography (silica gel//hexane/ethyl acetate).

Yield: 14.7 g of melting point 92°–95° C.,
IR (in KBr): 1738 cm$^{-1}$.

EXAMPLE 11

Preparation of methyl-8-[4,5-bis-(4-fluorophenyl)-1-phenyl-imidazol-2-yloxy]-caprylate, as described in Example 1 from 19.8 g of a 35% strength potassium hydride/mineral oil suspension, 60 g of 4,5-bis-(4-fluorophenyl)-1-phenyl-4-imidazolin-2-one, 700 ml of dimethylformamide and 41 g of methyl 8-bromocaprylate. Purification by column chromatography (silica gel//hexane/ethyl acetate).

Yield: 18.6 g of melting point 126°–128° C.,
IR (in KBr): 1740 cm$^{-1}$.

EXAMPLE 12

Preparation of methyl-8-[4,5-bis-(4-methoxyphenyl)-1-phenylimidazol-2-yloxy]-caprylate, as described in Example 1 from 41.5 g of a 35% strength potassium hydride/mineral oil suspension, 135 g of 4,5-bis-(4-methoxyphenyl)-1-phenyl-4-imidazolin-2-one, 800 ml of dimethylformamide and 86 g of methyl 8-bromocaprylate. Purification by column chromatography (silica gel//hexane/ethyl acetate).

Yield: 19 g of melting point 70°–72° C.,
IR (in KBr): 1738 cm$^{-1}$.

EXAMPLE 13

Preparation of methyl-8-[1,4,5-tris-(4-chlorophenyl)-imidazol-2-yloxy]-caprylate, as described in Example 1 from 31 g of a 35% strength potassium hydride/mineral oil suspension, 104 g of 1,4,5-tris-(4-chlorophenyl)-4-imidazolin-2-one, 600 ml of dimethylformamide and 65 g of methyl 8-bromocaprylate. Purification by column chromatography (silica gel//hexane/ethyl acetate).

Yield: 12.8 g of melting point 94°–96° C.,
IR (in KBr): 1739 cm$^{-1}$.

EXAMPLE 14

Preparation of methyl-11-(1,4,5-triphenylimidazol-2-yloxy)-undecanoate, as described in Example 1 from 36.3 g of a 35% strength potassium hydride/mineral oil suspension, 99 g of 1,4,5-triphenyl-4-imidazolin-2-one, 800 ml of dimethylformamide and 88 g of methyl-11-bromoundecanoate. Purification by column chromatography (silica gel//hexane/ethyl acetate).

Yield: 35 g of melting point 79°–80° C.,
IR (in KBr): 1740 cm$^{-1}$.

The following compounds are prepared as described in Examples 1 to 14 starting from the corresponding starting compounds: ethyl-1,4,5-triphenylimidazol-2-yloxyacetate, ethyl-3-(1,4,5-triphenylimidazol-2-yloxy)-propionate, methyl-8-[1-(3,4-dimethoxyphenyl)-4,5-diphenylimidazol-2-yloxy]-caprylate, methyl-9-(1,4,5-triphenylimidazol-2-yloxy)-pelargonate, ethyl-10-(1,4,5-triphenylimidazol-2-yloxy)-caprate and ethyl-8-(1,4,5-triphenylimidazol-2-yloxy)-caprylate.

EXAMPLE 15

Preparation of 8-(1,4,5-triphenylimidazol-2-yl-oxy)-caprylic acid.

171 g of methyl-8-(1,4,5-triphenylimidazol-2-yloxy)-caprylate and 44 g of sodium hydroxide are dissolved in 1,000 ml of methanol and the mixture is stirred at room temperature for about 24 hours. The solvent is then stripped off in vacuo and the residue is taken up in water. The aqueous solution is washed with ether and acidified with dilute hydrochloric acid and the acid precipitated is separated off and dried.

Yield: 151 g of melting point 165° C.,
MS[m/e]: 454 (19%), 312 (100%) and 180 (17%).

EXAMPLE 16

Preparation of 4-(1,4,5-triphenylimidazol-2-yloxy)-butyric acid, as described in Example 15 from 19.3 g of methyl-4-(1,4,5-triphenylimidazol-2-yloxy)butyrate and 3.6 g of sodium hydroxide in 500 ml of dioxane and 50 ml of water.

Yield: 19 g of melting point 142° C.,
MS [m/e]: 398 (0.8%) and 312 (38%).

EXAMPLE 17

Preparation of 5-(1,4,5-triphenylimidazol-2-yloxy)-valeric acid, as described in Example 15 from 28 g of ethyl-5-(1,4,5-triphenylimidazol-2-yloxy)-valerate and 7.5 g of sodium hydroxide in 400 ml of dioxane and 70 ml of water.

Yield: 26.1 g of melting point 140° C.,
MS [m/e]: 412 (2.6%) and 312 (33%).

EXAMPLE 18

Preparation of 6-(1,4,5-triphenylimidazol-2-yloxy)-caproic acid, as described in Example 15 from 28.5 g of ethyl-6-(1,4,5-triphenylimidazol-2-yloxy)caproate and 7.5 g of sodium hydroxide in 400 ml of dioxane and 70 ml of water.

Yield: 26.1 g of melting point 140°–145° C.,
MS [m/e]: 426 (0.9%), 312 (100%) and 180 (29%).

EXAMPLE 19

Preparation of 7-(1,4,5-triphenylimidazol-2-yloxy)-oenanthic acid, as described in Example 15 from 2 g of ethyl-7-(1,4,5-triphenylimidazol-2-yloxy)-oenanthate and 0.6 g of sodium hydroxide in 150 ml of ethanol.

Yield: 1.5 g of melting point 149° C.,
MS [m/e]: 440 (5%), 312 (100%) and 180 (32%).

EXAMPLE 20

Preparation of 8-[4,5-diphenyl-1-(4-methoxyphenyl)imidazol-2-yloxy]-caprylic acid, as described in Example 15 from 25 g of methyl-8-[4,5-diphenyl-1-(4-methoxyphenyl)-imidazol-2-yloxy]-caprylate and 8 g of sodium hydroxide in 250 ml of methanol.

Yield: 20 g of melting point 132°-133° C.,
MS [m/e]: 484 (2.9%), 342 (100%) and 210 (18%).

EXAMPLE 21

Preparation of 8-[1-(4-chlorophenyl)-4,5-diphenylimidazol-2-yloxy]-caprylic acid, as described in Example 15 from 17.1 g of methyl-8-[1-(4-chlorophenyl)-4,5-diphenylimidazol-2-yloxy]-caprylate and 4 g of sodium hydroxide in 350 ml of dioxane and 50 ml of water.

Yield: 14.5 g of melting point 118°-120° C.,
MS [m/e]: 488 (3.6%), 346 (100%), 310 (7%) and 214 (18%).

EXAMPLE 22

Preparation of 8-[4,5-diphenyl-1-(4-methylphenyl)imidazol-2-yloxy]-caprylic acid, as described in Example 15 from 5.5 g of methyl-8-[4,5-diphenyl-1-(4-methylphenyl)-imidazol-2-yloxy]-caprylate and 0.9 g of sodium hydroxide in 100 ml of dioxane and 10 ml of water.

Yield: 2.8 g of melting point 124° C.,
MS [m/e]: 468 (25%), 326 (100%) and 312 (19%).

EXAMPLE 23

Preparation of 8-[4,5-diphenyl-1-(2-fluorophenyl)imidazol-2-yloxy]-caprylic acid, as described in Example 15 from 10 g of methyl 8-[4,5-diphenyl-1-(2-fluorophenyl)imidazol-2-yloxy]-caprylate and 1.7 g of sodium hydroxide in 200 ml of dioxane and 40 ml of water.

Yield: 8.2 g of melting point 81° C.

EXAMPLE 24

Preparation of 8-[4,5-bis-(4-chlorophenyl)-1-phenylimidazol-2-yloxy]-caprylic acid, as described in Example 15 from 14.6 g of methyl-8-[4,5-bis-(4-chlorophenyl)-1-phenyl-imidazol-2-yloxy]-caprylate and 2.5 g of sodium hydroxide in 300 ml of dioxane and 40 ml of water.

Yield: 12.5 g of melting point 143°-145° C.,
MS [m/e]: 522 (0.7%), 380 (100%) and 214 (24%).

EXAMPLE 25

Preparation of 8-[4,5-bis-(4-fluorophenyl)-1-phenyl-imidazol-2-yloxy]-caprylic acid, as described in Example 15 from 18.5 g of methyl-8-[4,5-bis-(4-fluorophenyl)-1-phenyl-imidazol-2-yloxy]-caprylate and 3 g of sodium hydroxide in 400 ml of dioxane and 40 ml of water.

Yield: 14.5 g of melting point 155° C.,
MS [m/e]: 490 (13%), 348 (100%), 305 (4.2%) and 198 (18%).

EXAMPLE 26

Preparation of 8-[4,5-bis-(4-methoxyphenyl)-1-phenyl-imidazol-2-yloxy]-caprylic acid, as described in Example 15 from 8.44 g of methyl-8-[4,5-bis-(4-methoxyphenyl)-1-phenyl-imidazol-2-yloxy]-caprylate and 1.27 g of sodium hydroxide in 100 ml of dioxane and 10 ml of water.

Yield: 5 g of melting point 147°-149° C.,
MS [m/e]: 514 (0.8%), 372 (100%) and 357 (38%).

EXAMPLE 27

Preparation of 8-[1,4,5-tris-(4-chlorophenyl)imidazol-2-yloxy]-caprylic acid, as described in Example 15 from 12.8 g of methyl-8-[1,4,5-tris-(4-chlorophenyl)imidazol-2-yloxy]-caprylate and 3.6 g of sodium hydroxide in 450 ml of dioxane and 40 ml of water.

Yield: 9.6 g of melting point 133°-135° C.,
MS [m/e]: 416/M+-142, (100%)/, 378 (7%), 248 (13%), 138 (11%) and 111 (19%).

EXAMPLE 28

Preparation of 11-(1,4,5-triphenylimidazol-2-yloxy)-undecanoic acid, as described in Example 15 from 33 g of methyl-11-(1,4,5-triphenylimidazol-2-yloxy)-undecanoate and 6 g of sodium hydroxide in 800 ml of ethanol.

Yield: 28 g of melting point 107° C.,
MS [m/e]: 496 (1%), 312 (100%) and 180 (32%).

The following compounds are prepared as described in Examples 15 to 28 starting from the corresponding starting compounds: 1,4,5-triphenylimidazol-2-yloxyacetic acid, 3-(1,4,5-triphenylimidazol-2-yloxy)-propionic acid, 8-[1-(3,4-dimethoxyphenyl)-4,5-diphenylimidazol-2-yloxy]-caprylic acid, 9-(1,4,5-triphenylimidazol-2-yloxy)-pelargonic acid and 10-(1,4,5-triphenylimidazol-2-yloxy)-capric acid.

EXAMPLE 29

Preparation of sodium-8-(1,4,5-triphenylimidazol-2-yloxy)-caprylate.

8-(1,4,5-Triphenylimidazol-2-yloxy)-caprylic acid is dissolved in ethanol, the equivalent amount of ethanolic sodium hydroxide solution is added to the solution, the mixture is concentrated to dryness in vacuo and the residue is pulverised.

Yield: quantitative
IR (in KBr): 1553 cm$^{-1}$

The following sodium salts are prepared analogously to Example 29:

EXAMPLE 30

Sodium-1,4,5-triphenylimidazol-2-yloxyacetate,
IR (in KBr): 1615 cm$^{-1}$.

EXAMPLE 31

Sodium-3-(1,4,5-triphenylimidazol-2-yloxy)-propionate,
IR (in KBr): 1560 cm$^{-1}$.

EXAMPLE 32

Sodium 4-(1,4,5-triphenylimidazol-2-yloxy)-butyrate,
IR (in KBr): 1552 cm$^{-1}$.

EXAMPLE 33

Sodium-5-(1,4,5-triphenylimidazol-2-yloxy)-valerate,
IR (in KBr): 1554 cm$^{-1}$.

EXAMPLE 34

Sodium-6-(1,4,5-triphenylimidazol-2-yloxy)-caproate,
IR (in KBr): 1553 cm$^{-1}$.

EXAMPLE 35

Sodium-7-(1,4,5-triphenylimidazol-2-yloxy)-oenanthate
IR (in KBr): 1551 cm$^{-1}$.

EXAMPLE 36

Sodium-8-[4,5-diphenyl-1-(4-methoxyphenyl)-imidazol-2-yloxy]-caprylate,
IR (in KBr): 1551 cm$^{-1}$.

EXAMPLE 37

Sodium-8-[1-(4-chlorophenyl)-4,5-diphenylimidazol-2-yloxy]-caprylate,
IR (in KBr): 1555 cm$^{-1}$

EXAMPLE 38

Sodium-8-[4,5-diphenyl-1-(4-methylphenyl)-imidazol-2-yloxy]-caprylate
IR (in KBr): 1553 cm$^{-1}$.

EXAMPLE 39

Sodium-8-[4,5-diphenyl-1-(2-fluorophenyl)-imidazol-2-yloxy]-caprylate,
IR (in KBr): 1555 cm$^{-1}$.

EXAMPLE 40

Sodium-8-[4,5-bis-(4-chlorophenyl)-1-phenyl-imidazol-2-yloxy]-caprylate,
IR (in KBr): 1560 cm$^{-1}$.

EXAMPLE 41

Sodium-8-[4,5-bis-(4-fluorophenyl)-1-phenyl-imidazol-2-yloxy]-caprylate,
IR (in KBr): 1556 cm$^{-1}$.

EXAMPLE 42

Sodium-8-[4,5-bis-(4-methoxyphenyl)-1-phenyl-imidazol-2-yloxy]-caprylate,
IR (in KBr): 1553 cm$^{-1}$.

EXAMPLE 43

Sodium-8-[1,4,5-tris-(4-chlorophenyl)-imidazol-2-yloxy]-caprylate,
IR (in KBr): 1563 cm$^{-1}$.

EXAMPLE 44

Sodium-8-[1-(3,4-dimethoxyphenyl)-4,5-diphenyl-imidazol-2-yloxy]-caprylate,
IR (in KBr): 1555 cm$^{-1}$.

EXAMPLE 45

Sodium-9-(1,4,5-triphenylimidazol-2-yloxy)-pelargonate,
IR (in KBr): 1558 cm$^{-1}$.

EXAMPLE 46

Sodium-10-(1,4,5-triphenylimidazol-2-yloxy)-caprate,
IR (in KBr): 1560 cm$^{-1}$.

EXAMPLE 47

Sodium-11-(1,4,5-triphenylimidazol-2-yloxy)-undecanoate,
IR (in KBr): 1565 cm$^{-1}$.

EXAMPLE 48

Preparation of hexyl-8-(1,4,5-triphenylimidazol-2-yloxy)-caprylate.

4.8 g of sodium-8-(1,4,5-triphenylimidazol-2-yloxy-caprylate, 1.2 g of 1-chlorohexane and 0.2 g of sodium iodide in 20 ml of dimethylformamide are heated at 80° C. for 8 hours. After cooling, the mixture is diluted with water and extracted with chloroform. The chloroform solution is washed successively with water, 5% strength sodium bicarbonate solution and water, dried over sodium sulphate and concentrated in vacuo. The residue is purified by column chromatography (silica gel//hexane/ethyl acetate).

Yield: 4.1 g of melting point 92° C.
IR (in KBr): 1726 cm$^{-1}$.

EXAMPLE 49

Preparation of benzyl 8-(1,4,5-triphenylimidazol-2-yloxy)-caprylate, as described in Example 48 from 4.8 g of sodium-8-(1,4,5-triphenylimidazol-2-yloxy)-caprylate, 1.3 g of benzyl chloride and 0.2 g of sodium iodide in 20 ml of dimethylformamide.

Yield: 4.6 g of melting point 95° C.,
IR (in KBr): 1731 cm$^{-1}$.

What we claim is:

1. ω-(1,4,5-Triphenylimidazol-2-yloxy)-alkanoic acids and their derivatives of the general formula I

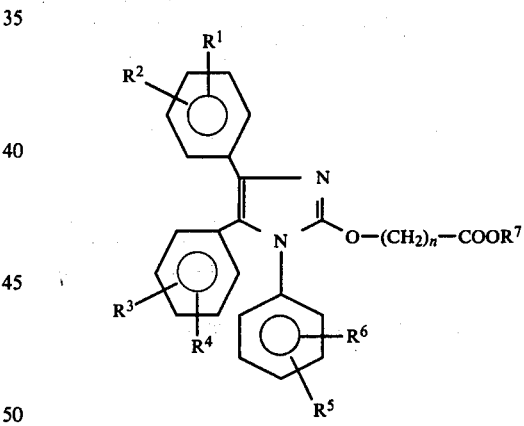

wherein n is an integer from 1 to 10, $R^1$, $R^2$, $R^3$, $R^4$, $R^5$ and $R^6$, which are identical or different from each other, are members selected from the group consisting of hydrogen, the halogens, alkyl, alkoxy and trifluoromethyl, and one or several of the groupments $R^1$ and $R^2$, $R^3$ and $R^4$, and $R^5$ and $R^6$ together, a methylenedioxy group, and $R^7$ is a member selected from the group consisting of hydrogen, the alkali metal ions, the straight-chain and the branched alkyl group with 1 to 6 carbon atoms and the benzyl group.

2. The ω-(1,4,5-triphenylimidazol-2-yloxy)-alkanoic acids and their derivatives of the general formula I as claimed in claim 1 wherein $R^1$, $R^2$, $R^3$, $R^4$, $R^5$ and $R^6$, which are identical or different from each other, are members selected from the group consisting of hydrogen, methyl, ethyl, n- and isopropyl, fluorine, chlorine, bromine, methoxy and ethoxy.

3. 1,4,5-Triphenylimidazol-2-yloxyacetic acid and pharmaceutically acceptable salts and esters thereof.

4. 4-(1,4,5-Triphenylimidazol-2-yloxy)-butyric acid and pharmaceutically acceptable salts and esters thereof.

5. 5-(1,4,5-Triphenylimidazol-2-yloxy)-valeric acid and pharmaceutically acceptable salts and esters thereof.

6. 6-(1,4,5-Triphenylimidazol-2-yloxy)-caproic acid and pharmaceutically acceptable salts and esters thereof.

7. 7-(1,4,5-Triphenylimidazol-2-yloxy)-oenanthic acid and pharmaceutically acceptable salts and esters thereof.

8. 8-(1,4,5-Triphenylimidazol-2-yloxy)-caprylic acid and pharmaceutically acceptable salts and esters thereof.

9. 8-[4,5-Diphenyl-1-(4-methoxyphenyl)-imidazol-2-yloxy]-caprylic acid and pharmaceutically acceptable salts and esters thereof.

10. 8-[1-(4-Chlorophenyl)-4,5-diphenylimidazol-2-yloxy]-caprylic acid and pharmaceutically acceptable salts and esters thereof.

11. 8-[4,5-Diphenyl-1-(4-methylphenyl)-imidazol-2-yloxy]-caprylic acid and pharmaceutically acceptable salts and esters thereof.

12. 8-[4,5-Diphenyl-1-(2-fluorophenyl)-imidazol-2-yloxy]-caprylic acid and pharmaceutically acceptable salts and esters thereof.

13. 8-[4,5-bis-(4-Chlorophenyl)-1-phenyl-imidazol-2-yloxy]-caprylic acid and pharmaceutically acceptable salts and esters thereof.

14. 8-[4,5-bis-(4-Fluorophenyl)-1-phenyl-imidazol-2-yloxy]-caprylic acid and pharmaceutically acceptable salts and esters thereof.

15. 8-[4,5-bis-(4-Methoxyphenyl)-1-phenyl-imidazol-2-yloxy]-caprylic acid and pharmaceutically acceptable salts and esters thereof.

16. 8-[1,4,5-tris-(4-Chlorophenyl)-imidazol-2-yloxy]-caprylic acid and pharmaceutically acceptable salts and esters thereof.

17. 8-[1-(3,4-Dimethoxyphenyl)-4,5-diphenyl-imidazol-2-yloxy]-caprylic acid and pharmaceutically acceptable salts and esters thereof.

18. 9-(1,4,5-Triphenylimidazol-2-yloxy)-pelargonic acid and pharmaceutically acceptable salts and esters thereof.

19. 10-(1,4,5-Triphenylimidazol-2-yloxy)-capric acid and pharmaceutically acceptable salts and esters thereof.

20. 11-(1,4,5-Triphenylimidazol-2-yloxy)-undecanoic acid and pharmaceutically acceptable salts and esters thereof.

21. Process for the treatment of thromboembolic, inflammatory and/or atherosclerotic diseases in humans by administering to humans suffering from such diseases a compound as claimed in claim 1 or claim 2 or in any of claims 3 to 20 once or several times per day in a dose amounting to from 1 to 1,000 mg per dose.

* * * * *